(12) United States Patent
Jung

(10) Patent No.: US 9,045,362 B2
(45) Date of Patent: Jun. 2, 2015

(54) BIOACTIVE GLASS SCAFFOLDS, AND METHOD OF MAKING

(71) Applicant: MOSCI CORP., Rolla, MO (US)

(72) Inventor: Steven Jung, Rolla, MO (US)

(73) Assignee: MOSCI CORP., Rolla, MO (US)

( * ) Notice: Subject to any disclaimer, the term of this patent is extended or adjusted under 35 U.S.C. 154(b) by 326 days.

(21) Appl. No.: 13/836,207

(22) Filed: Mar. 15, 2013

(65) Prior Publication Data

US 2014/0272418 A1  Sep. 18, 2014

(51) Int. Cl.
  *C03B 19/06* (2006.01)
  *C03B 19/10* (2006.01)
  *C03C 4/00* (2006.01)

(52) U.S. Cl.
  CPC ........... *C03C 4/0007* (2013.01); *Y10T 428/315* (2015.01)

(58) Field of Classification Search
  CPC ........ C03B 19/01; C03B 19/06; C03B 19/10; C03B 19/1005; C03B 19/1055; C03B 19/108; C03B 19/1085; C03B 19/109; C03C 4/007
  USPC .................................................. 65/17.4, 21.4
  See application file for complete search history.

(56) References Cited

U.S. PATENT DOCUMENTS

| | | | |
|---|---|---|---|
| 4,340,627 A | 7/1982 | Herzog et al. | |
| 4,867,931 A | 9/1989 | Cochran | |
| 5,514,378 A | 5/1996 | Mikos et al. | |
| 6,054,400 A * | 4/2000 | Brink et al. | 501/63 |
| 6,254,981 B1 | 7/2001 | Castle | |
| 6,309,423 B2 | 10/2001 | Hayes | |
| 6,406,498 B1 | 6/2002 | Tormala et al. | |
| 6,720,007 B2 | 4/2004 | Walt et al. | |
| 6,974,862 B2 | 12/2005 | Ringeisen et al. | |
| 7,964,538 B2 | 6/2011 | Perera et al. | |
| 8,047,288 B2 | 11/2011 | Skala et al. | |
| 8,389,017 B1 | 3/2013 | Starling et al. | |
| 8,449,904 B1 * | 5/2013 | Jung | 424/423 |
| 8,883,195 B2 * | 11/2014 | Bagga et al. | 424/443 |
| 8,889,178 B2 * | 11/2014 | Bagga et al. | 424/443 |
| 2003/0206928 A1 | 11/2003 | Tormala et al. | |

(Continued)

FOREIGN PATENT DOCUMENTS

WO   WO 2012/040025   3/2012

OTHER PUBLICATIONS

International Search Report for related PCT Patent App. No. PCT/US13/36418 dated Aug. 12, 2013.

(Continued)

*Primary Examiner* — Jason L Lazorcik
(74) *Attorney, Agent, or Firm* — Husch Blackwell LLP

(57) ABSTRACT

A glass, glass-ceramic, or ceramic bead is described, with an internal porous scaffold microstructure that is surrounded by an amorphous shield. The shield serves to protect the internal porous microstructure of the shield while increasing the overall strength of the porous microstructure and improve the flowability of the beads either by themselves or in devices such as biologically degradable putty that would be used in bone or soft tissue augmentation or regeneration. The open porosity present inside the bead will allow for enhanced degradability in-vivo as compared to solid particles or spheres and also promote the growth of tissues including but not limited to all types of bone, soft tissue, blood vessels, and nerves.

10 Claims, 5 Drawing Sheets

(56) References Cited

U.S. PATENT DOCUMENTS

Figure 1:
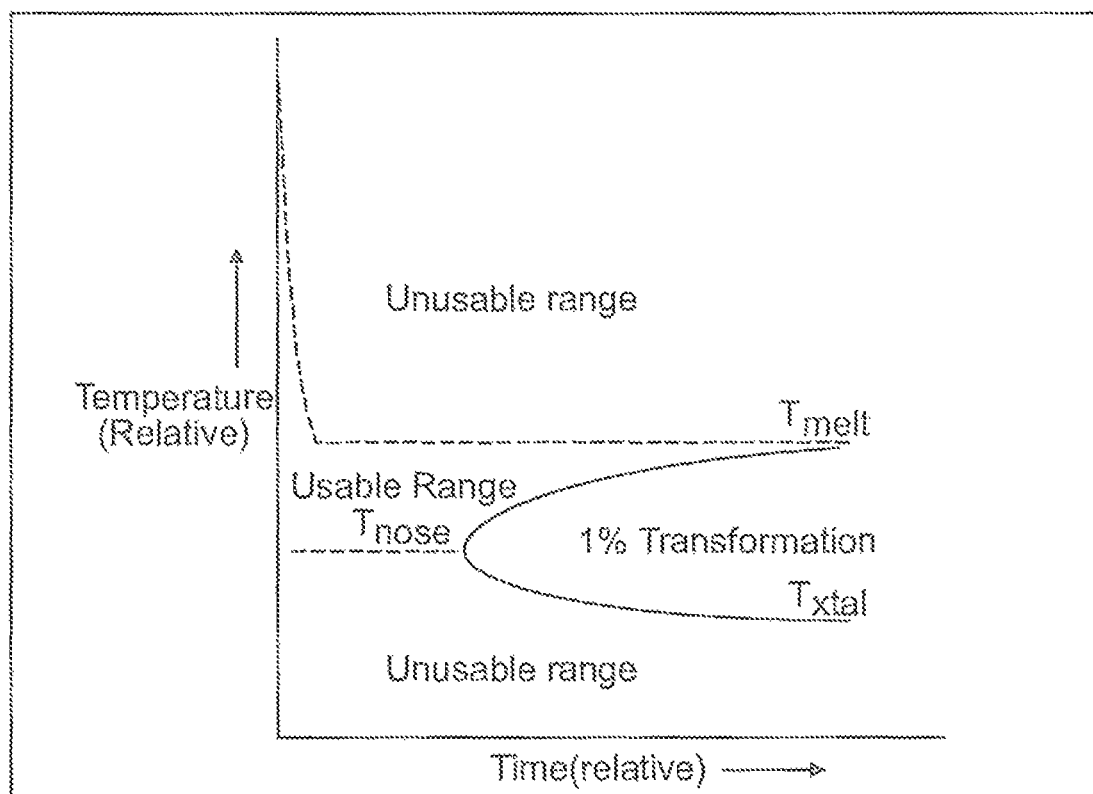

| | | | |
|---|---|---|---|
| 2008/0060382 A1* | 3/2008 | Rake et al. ............... | 65/21.2 |
| 2010/0136086 A1 | 6/2010 | Day et al. | |
| 2010/0179667 A1 | 7/2010 | Day et al. | |
| 2010/0249913 A1 | 9/2010 | Datta et al. | |
| 2011/0014261 A1* | 1/2011 | Day et al. ............... | 424/423 |
| 2011/0014262 A1* | 1/2011 | Jung et al. ............... | 424/423 |
| 2011/0106255 A1 | 5/2011 | Liu et al. | |
| 2011/0106272 A1* | 5/2011 | Liu ............... | 623/23.61 |
| 2011/0133368 A1 | 6/2011 | Ringeisen et al. | |
| 2011/0143044 A1 | 6/2011 | Bujard et al. | |
| 2011/0144763 A1 | 6/2011 | Bagga et al. | |
| 2011/0144764 A1 | 6/2011 | Bagga et al. | |
| 2011/0165217 A1* | 7/2011 | Jung et al. ............... | 424/423 |
| 2011/0206828 A1* | 8/2011 | Liu et al. ............... | 427/2.24 |
| 2011/0217388 A1* | 9/2011 | Greenspan et al. ........... | 424/602 |
| 2013/0014945 A1 | 1/2013 | Fang et al. | |
| 2013/0101673 A1* | 4/2013 | Borden ............... | 424/492 |
| 2013/0228947 A1* | 9/2013 | Liu et al. ............... | 264/49 |

OTHER PUBLICATIONS

Lu, H. et al., "Electrospun submicron bioactive glass fibers for bone tissue scaffold," J. Mater Sci: Mater Med 20: 793-798 (2009).

Kim, H.W. et al., "Production and potential of Bioactive Glass Nanofibers as a Next-generation Biomaterial," Adv. Funct. Mater. 16:1529-1535 (2006).

Rahaman, M., et al., Acra Biomateriala 7:2355-2373 (2011).

Oh et al., Bioceramics for Tissue Engineering Applications—A Review; American Journal of Biochemistry and Biotechnology 2 (2): 49-56, 2006.

Boccaccini et al., Sintering,c rystallisation and biodegradation behaviour of Bioglass—derived glass-ceramics; The Royal Society of Chemistry 2007; 27-44.

Chen et al., 45S5 Bioglass-derived glass-ceramic scaffold for bone tissue engineering; Elsevier Ltd 2005; 2414-2425.

Srivastava et al., In Vitro Bioactivity and Physical-Mechanical Properties of $Fe_2O_3$ substituted 45S5 Bioactive Glasses and Gladd—ceramics; Internatonal Jounral of Scientific & Engineering Research, vol. 3, Issue 2, Feb. 2012; 15 pages total.

Bellucci, et al., Shell Scaffolds: A new approach towards high strength bioceramic scaffold for bone regeneration; Materials Letters 64 (2010) 203-206.

Liu et al., Bioactive Borosilicate Glass Scaffolds: improvement on the strength of glass-based scaffold for tissue engineering; J. Mater Sci: Mater Med (2009) 20:365-372.

Jung et al., Conversion Kinetics of Silicate, borosilicate, and borate bioactive glasses ti hydroyapatite; Phys. Chem. Glasses: Eur. J. Glass Sci. Technol. B, Apr. 2009, 50(2), 85-88.

Rahaman et al., Bioactive glass in tissue engineering; Acta Materialia Inc. published by Elseview Ltd 2011; 2355-2373.

* cited by examiner

BIOACTIVE GLASS SCAFFOLDS, AND METHOD OF MAKING

FIELD OF THE INVENTION

This invention relates to a biocompatible scaffold for implantation into mammals to facilitate tissue repair and tissue regeneration.

BACKGROUND OF THE INVENTION

Porous bioactive glass scaffolds have been of interest for biomaterial design for some time. A microstructure that can stimulate the healing process and promote tissue growth while being made from a material that will eventually degrade is attractive. Unfortunately, highly porous materials inherently have low strength which can be a major detriment. Another major hurdle to be overcome is the poor handleability of porous scaffolds as they easily break when handled, can easily get tangled together, and ultimately become ineffective for the intended purpose. The majority of the orthopedic industry uses dense particles of cadaver bone, calcium phosphate based ceramics, or bioactive glass in their devices as they have the required strength and handleability required during surgery.

The use of silicate based bioactive glasses such as 45S5 and S53P4, are currently used in products approved by the US Food and Drug Administration and other world safety organizations for use in implantable devices such as orthopedic implants and are known to be capable of making three dimensional porous scaffolds. Glasses with compositions similar to 45S5 and S53P4 crystallize rapidly when heated above each glasses respective glass transition temperature ($T_g$), making viscous sintering by traditional heat treatments difficult without crystallization. Therefore, currently there are no amorphous, rigid, and porous scaffolds composed of silicate glasses are commercially available. Glasses with wider working ranges with multiple alkali and alkaline earth elements in combination with additional silica have been developed to fill the need, but these glasses convert to hydroxyl apatite (HA) slower than 45S5 and S53P4, and none of these scaffolds are in currently available products approved by the FDA for any clinical market.

Silicate glass particles that are larger than >500 µm can take years to fully react with body fluids and be converted to the inorganic component of bone known as hydroxyapatite (HA) because, large particles of glass (>500 µm) leave voids in healing tissue that take years to remodel into natural tissue, and the large particles have a relatively small surface area mass ratio and don't allow for tissue penetration by bone or blood vessels.

Porous scaffolds allow for tissue penetration, and the surface area available for reaction with body fluids is relatively large and penetrates throughout the entire scaffold, which significantly reduces conversion time to HA and final remodeling. The conversion kinetics of silicate glass 45S5 to HA has been shown to slow from the contracting volume model to the diffusion model once the silica gel layer achieves a thickness great enough to become the diffusion barrier. This is the reason why a porous scaffold composed of 45S5 will convert to HA in a matter of weeks as opposed to a solid glass 45S5 bead of comparable size that could take years.

The crystallization properties and glass transition properties of a particular glass are important when treating glass and making it into a porous scaffold. Glass compositions composed of relatively low concentrations of glass forming oxides and relatively high concentrations of alkaline and alkaline earth oxides tend to crystallize rapidly when heated above the glass transition temperature, making bonding by viscous flow difficult. Therefore the ability to make porous materials or scaffolds rigid from these glasses by traditional thermal treatments has not been possible.

Typically, glass is bonded by heating above the glass transition temperature to a viscosity appropriate for viscous flow. Depending on the amount of time allowable for the process and the amount of flow required, the viscosity used for processing can vary with the application. Glasses used for such applications are designed to resist crystallization at the processing temperatures because the mobility of ions is high. The more fluid the glass, typically the easier it may be for a glass to crystallize, but this is dependent on how close the glass composition is to a crystalline phase and how great the activation energy is to allow the glass to crystallize.

The glasses that will benefit from this method of bonding require relatively low energy input to allow the atoms to rearrange and start forming crystals. The formation of crystals, especially at the particle surface, is what inhibits the viscous flow of these particles. Crystalline phases that crystallize from glass typically melt at significantly higher temperatures than the temperatures required for crystallization; therefore the crystals do not form a viscous flow that would aid in the sintering process. In addition, the tendency towards crystallization increases as the surface area to volume ratio of the glass component increases, so the smaller the component, the greater the tendency toward surface crystallization and inhibited bonding.

Scaffolds, particularly those designed for use as bone grafts, should be highly porous (>50%) and are often formed by infusing a slurry composed of glass particles and other organic and inorganic components into a preform (foam or sponge or other porous polymer) that must be slowly burned out prior to sintering. To keep the desired microstructure of the preform, the heating rate is typically kept low, a few ° C./min, to the sintering temperature, and then the sintered part is slow cooled as to eliminate thermal shock of the glass/ceramic scaffold. For glasses that crystallize quickly (45S5 and S53P4), these methods are not effective in making rigid glass scaffolds.

The graph shown in FIG. 1 describes the usable regions of interest for the possible heat treatments of the following invention. Sintering bioactive glass is a time-temperature-crystallization dependent process, and no single component can be ignored.

Typically, scaffolds discussed in the literature are rough and sharp, which is not an issue for bench scale testing, but can be a significant problem for clinicians such as orthopedic surgeons that want to press on the implant material without puncturing a glove. A punctured glove opens the clinician and the patient up to possible disease transmission, and the clinician could be injured by the implant material if it were to penetrate the clinician's skin. Therefore, no fully amorphous scaffolds composed of silicate based 45S5 or S53P4 bioactive glass are currently approved for by the FDA for clinical use.

The surface roughness of a scaffold is certainly a disadvantage from a handling point of view, but in a product such as bone putty or even just a single phase implant material such as loose granules, the rough edges make each scaffold catch on one another decreasing the flowability of the particles. This decrease in flowability decreases the overall scaffold loading the putty can incorporate as the putty itself acts as a lubricant to improve the handleability. The debris from broken edges may also increase the overall immune response as macrophages try to remove/engulf the small particles.

Therefore a need exists for a method of bonding of silicate based bioactive glass with a high affinity for crystallization.

SUMMARY OF THE INVENTION

One concept of the invention is a glass, glass-ceramic, or ceramic bead with an internal porous scaffold microstructure that is surrounded by an amorphous shield and prepared without a volatile component, or binder and pore former. The shield serves to protect the internal porous microstructure of the shield while increasing the overall strength of the porous microstructure and improve the flowability of the beads either by themselves or in devices such as biologically degradable putty that would be used in bone or soft tissue augmentation or regeneration. The open porosity present inside the bead will allow for enhanced degradability in-vivo as compared to solid particles or spheres and also promote the growth of tissues including but not limited to all types of bone, soft tissue, blood vessels, and nerves. A few examples of the internal microstructure are directionally oriented or randomly oriented network of fibers, randomly oriented network of fibers mixed with glass beads, or it can be composed of interconnected pores formed by the partial fusing of glass particles. The shielded scaffolds may comprise one or more glass compositions for purposes of controlling degradation, biological stimulation, or antimicrobial properties to name a few.

The subject invention involves a method that packages the porous scaffold and retains the desired degradability and porous microstructure of a scaffold in an encapsulated shell that increases the scaffold strength and lubricity prior to implantation and improves handleability when used as a standalone graft material or a component of a putty. Thus, protecting the bioactive glass scaffold microstructure can be effected prior to and during the implantation and will enhance the microstructures available in markets such as orthopedic, spine, and soft tissue wound healing.

In the practice of the subject invention, a powder of bioactive glass is crushed and wetted. The wetted powder is mixed to make the wet particles stick together and form agglomerates, which may then be sintered or used as putty. Another embodiment is composed of sintered fiber granules made by a similar method, i.e., fiber balls are made by mixing glass fibers and glass beads and vibrating, which in turn forms interlocking structures that are then placed in a ceramic crucible for heat treatment. The resulting porous rigid granule comprises of sintered fibers and beads. Another embodiment uses the previously mentioned interlocking fibers and beads and flame sinters the granules by dropping the interlocking structures through a flame which forms a relatively smooth porous shield surrounding a core of unbound or loose fibers and beads. Another embodiment involves sintering the particulate or fiber scaffold in a crucible first, then heating in a flame to form a surface layer shield, and once it has passed through the flame and collected it is ready for use.

CONCISE DESCRIPTION OF THE DRAWINGS

Figure 2:
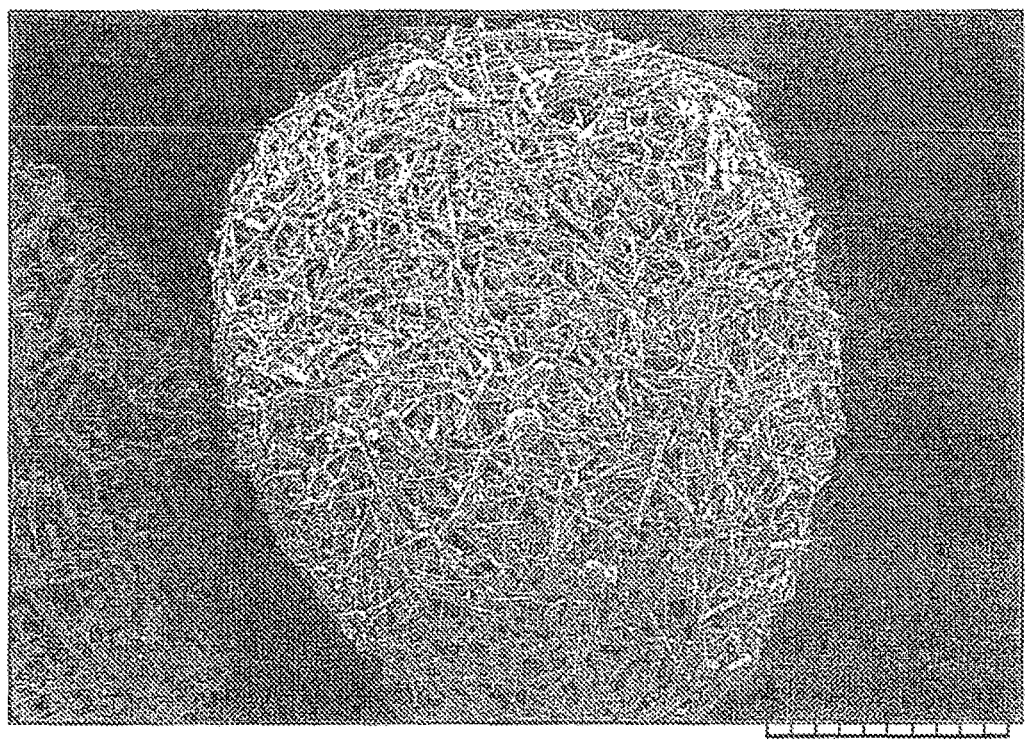
Figure 3:
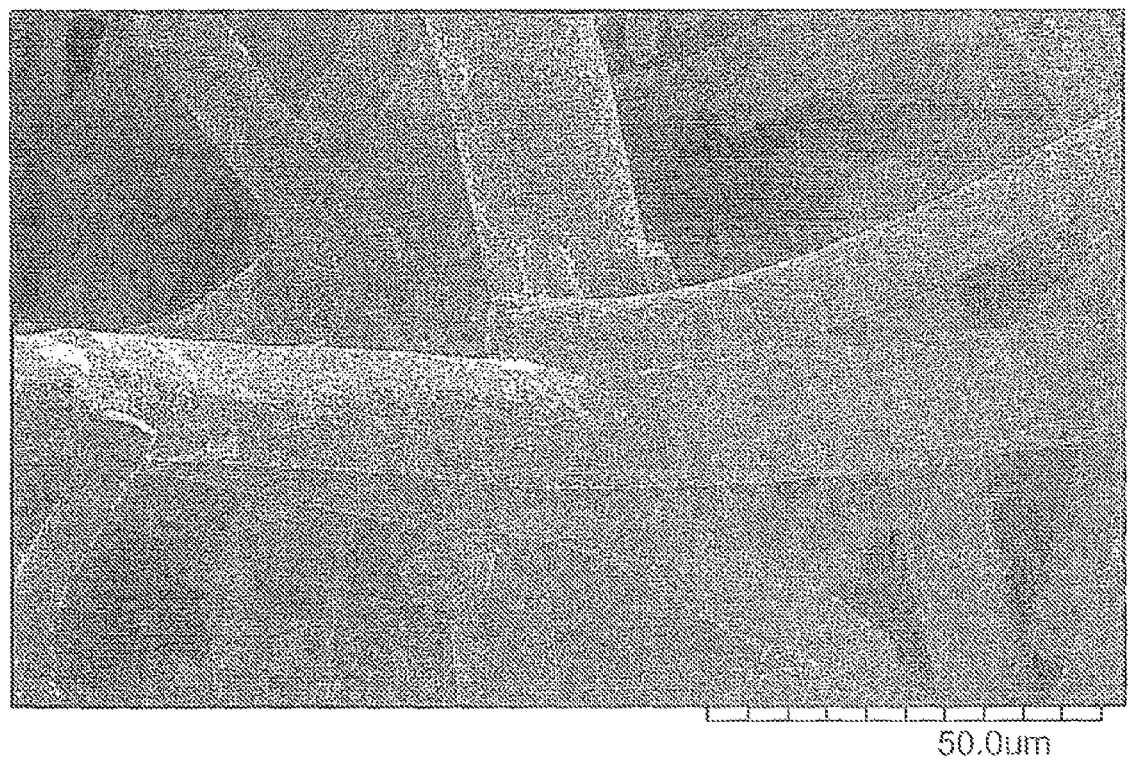
Figure 4:
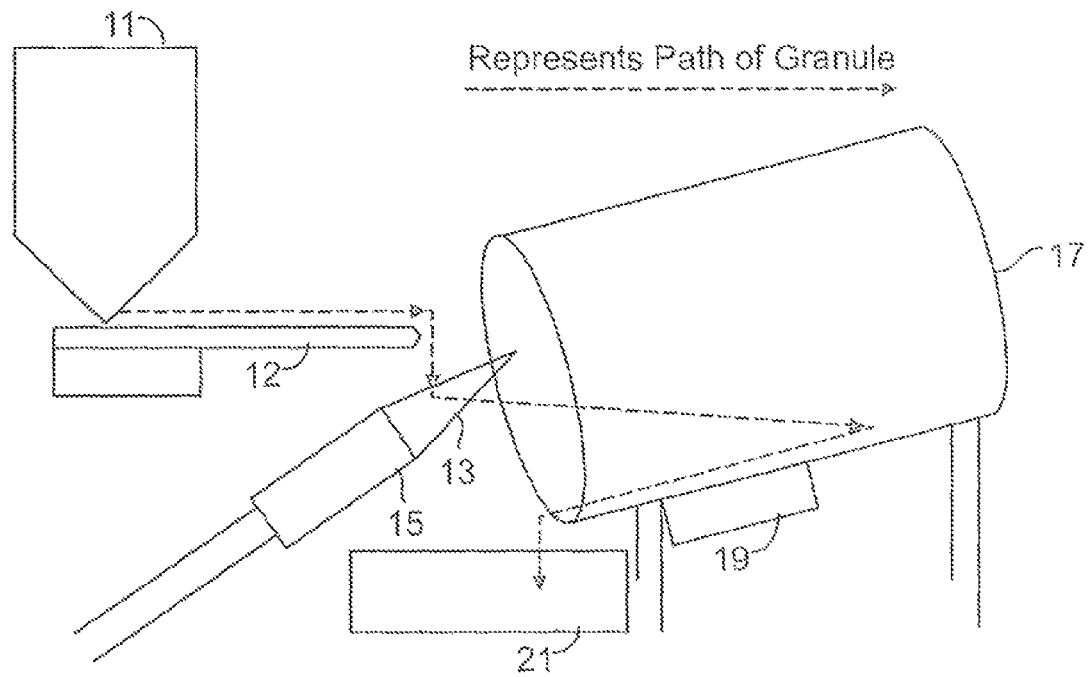
Figure 5:
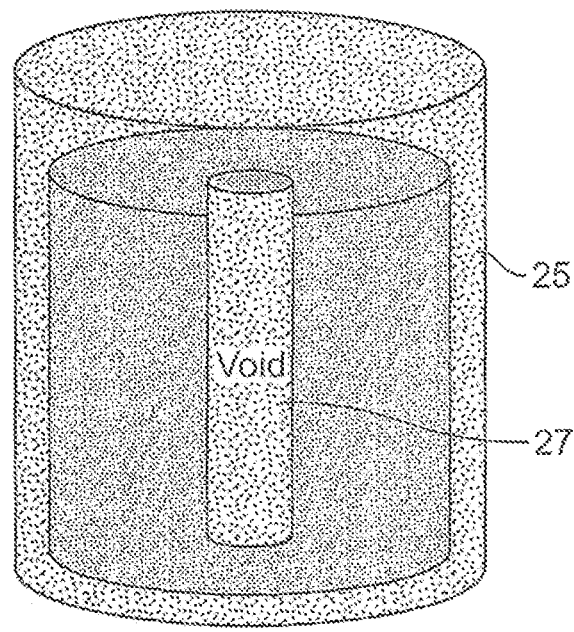
Figure 6:
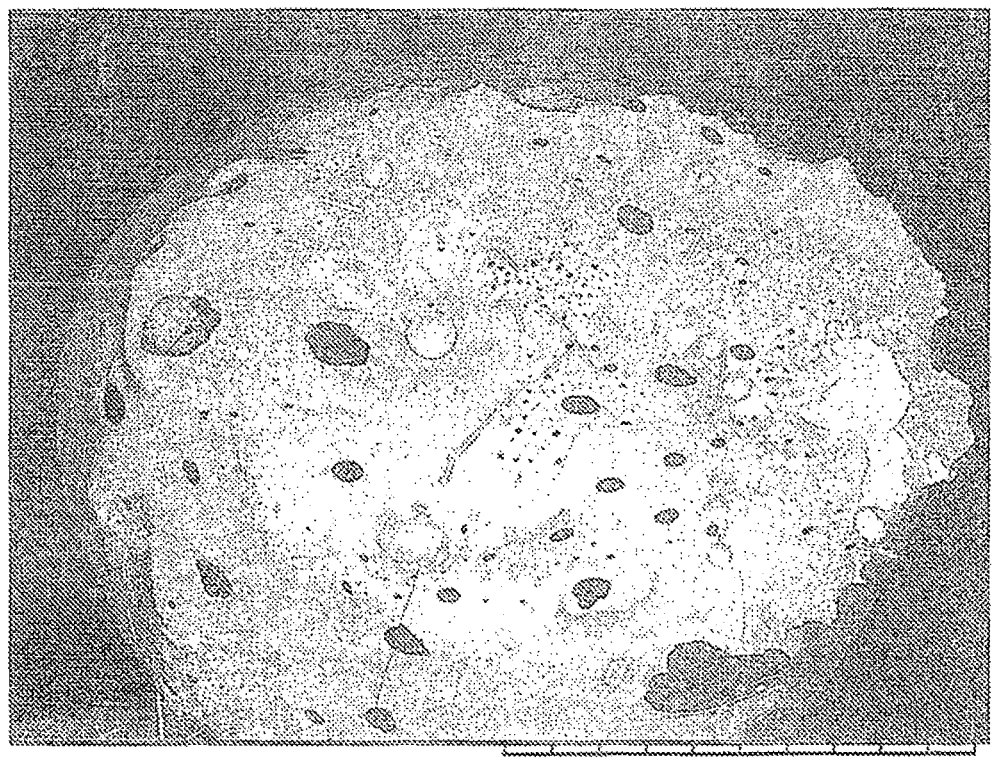
Figure 7:
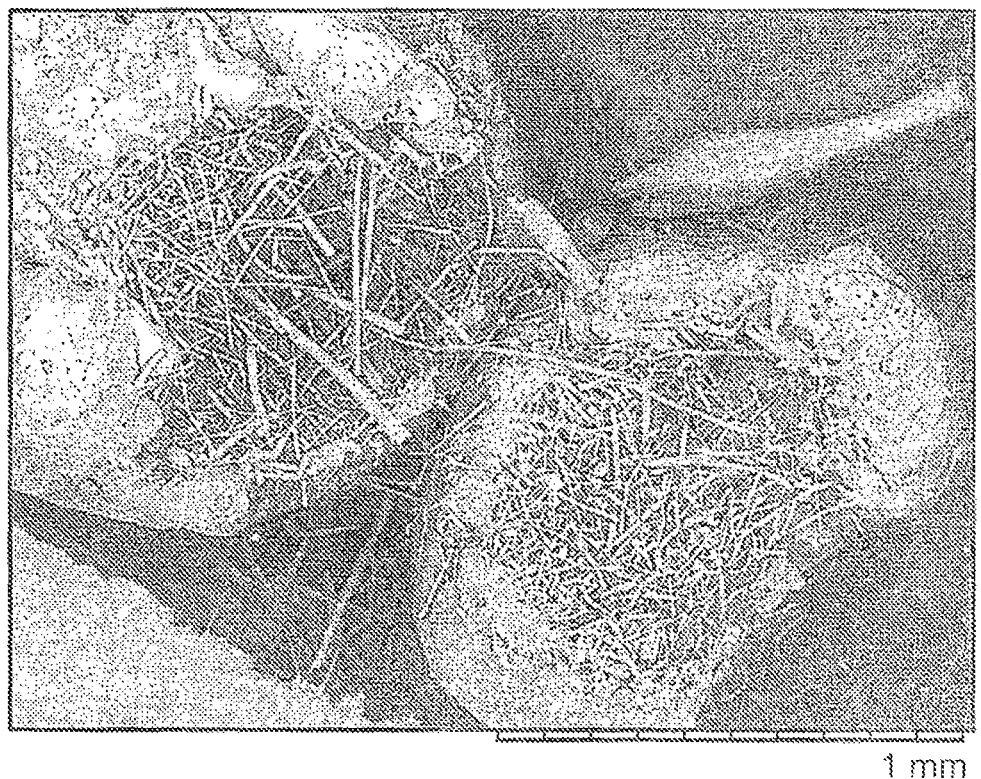
Figure 8:
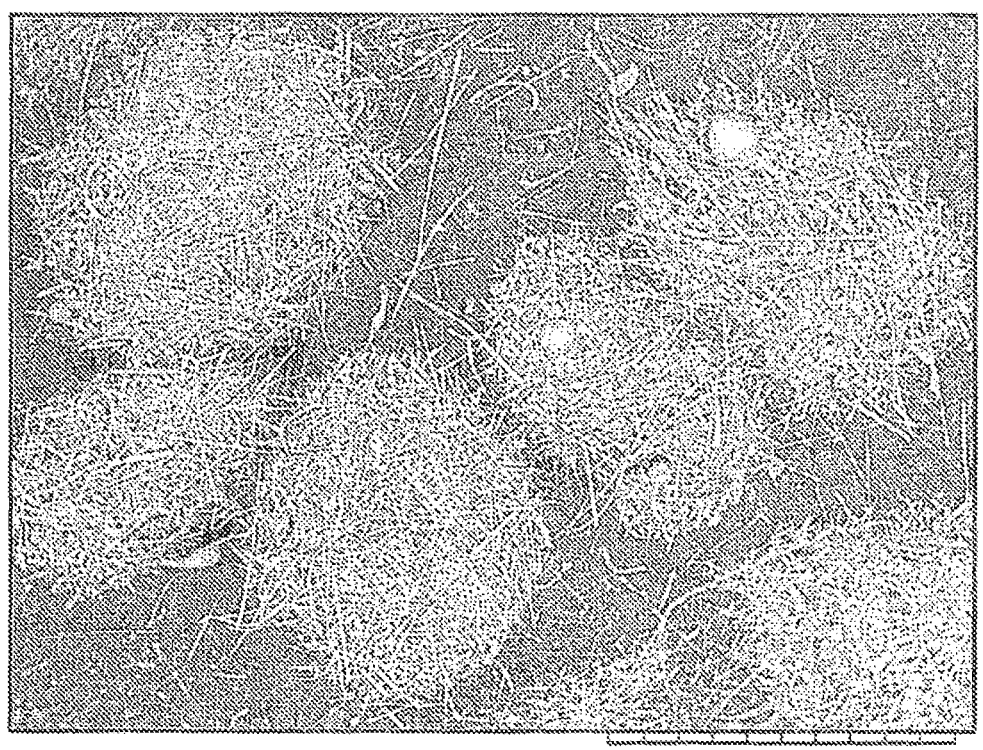
Figure 9:
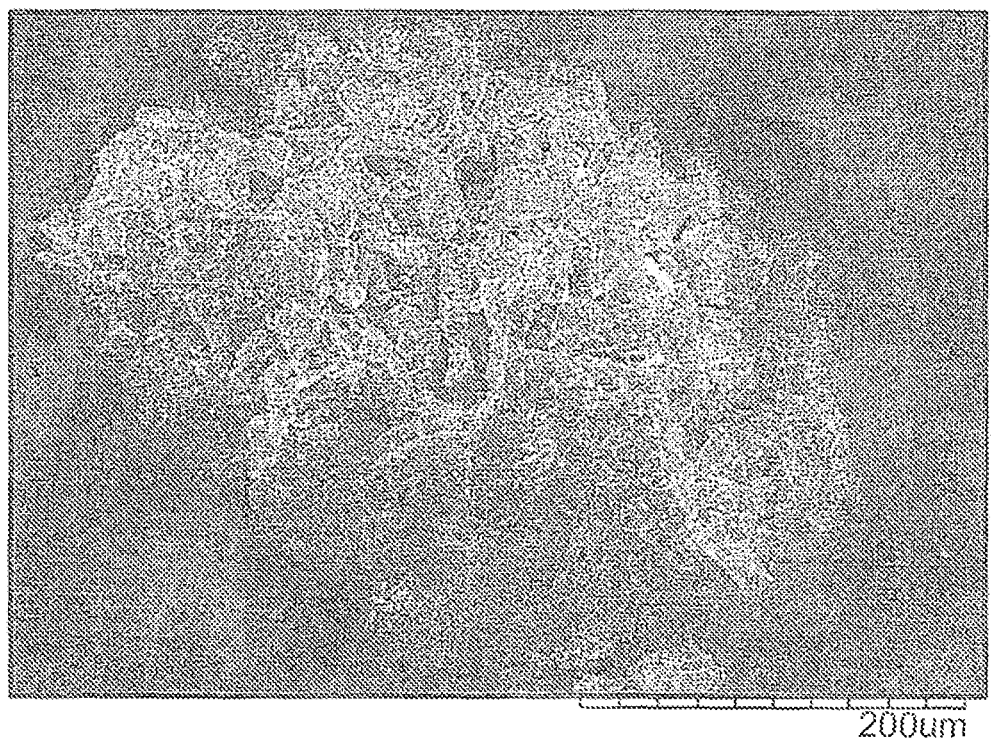

FIG. 1 is a graph of a glass transformation curve.
FIG. 2 is a picture of a sintered glass fiber/bead scaffold particle.
FIG. 3 is a magnified view of the surface of the scaffold particle of FIG. 2.
FIG. 4 is a schematic of the apparatus used in the method of the subject invention.
FIG. 5 is a graphic of a crucible holding agglomerates with a void in the middle.
FIG. 6 is a picture of a sintered and fused fiber/bead granule.
FIG. 7 is a picture of the fiber/bead granule of FIG. 6 cut in half.
FIG. 8 is a picture of a number of unsintered particulate scaffold balls.
FIG. 9 is a picture of a sintered bead scaffold particle.

DETAILED DESCRIPTION OF THE DRAWINGS

Scaffolds for tissue engineering can be formed from bioactive glass. Bioactive glass can be Silicate bioactive glass, Borate bioactive glass or Phosphate bioactive glass. While all these glasses may be used in the subject invention, Silicate bioactive glass, such as 45S5 and S53P4 is preferred. Silicate bioactive glass generally has a composition of sodium carbonate, calcium carbonate, phosphorus pentoxide and silica, such as a glass composition having about 45-60 mol % silica and a 2-10 molar ratio of calcium to phosphate. Glass materials having this or a similar composition, demonstrate the formation of a silica-rich layer and a calcium phosphate film on the materials surface in an aqueous environment that readily bonds the glass material to bone. Compositional variations can be made, through the addition of compositions such as magnesia, potassium oxide, boric oxide, and other compounds, though it is generally known that a silica content between 45-60 mol % at the interfacial layer is advantageous to the formation of the silica-rich layer with the calcium phosphate film to promote the formation of bonds between the scaffold, the natural bone and soft tissue materials.

Glass compounds are more easily formed into a fiber when the material can be melted and drawn into a fiber while amorphous. Bioactive and bioresorbable materials that can be fabricated into a fiber form without devitrification during the fiber drawing process require high silica content and both sodium oxide and potassium oxide to provide a mixed alkali effect to maintain an amorphous structure when drawn into a fiber. Various compounds of mixed alkali and high-silica content glasses that can be easily pulled into fibers have demonstrated both bioactivity and bioresorbability.

The first step in crystallizing a glass is the formation of nuclei in the glass. Nuclei can be formed by imperfections in the glass such as on a surface, or by thermal treatments. Numerous studies exist for the nucleation and growth of glass ceramics, and in particular the $Na_2Ca_2Si_3O_9$ glass is of interest since this is the phase 45S5 when crystallized. The glass is heated quickly (a minimum of ~300 to 400° C./min upwards of 200,000° C./sec heat rate) through the nucleation temperature range so as to suppress nucleation and crystal growth, therefore allowing viscous flow to occur between the particles for a short time (<1 sec to 10 to 20 min), and then cooling again at a rate ~1000 to 2500° C./min to 200,000° C./sec. This method of fast heating and cooling reduces the crystallization effects of a glass with high crystallization affinity and allows for the formation of a porous scaffold.

Each component of the fiber/bead un-sintered scaffold (fibers and beads) on its own is a flowable material made of individual fibers or beads. When the two are put together, crushed to a size of about 25 μm, and lightly shaken, the fibers and beads interlock, forming balls that are approximately 0.5 to 4 mm in diameter, are soft to the touch, yet compressible as shown in FIG. 8. The compressibility comes from the individual glass components which are much stronger individually than if the individual components were lightly sintered, or bonded together with a polymeric phase as other bioactive glass scaffolds known in the art. The individual glass components can move and reconstitute; which is a significant advantage over traditional scaffold materials.

It is also possible to use only glass particles, which are crushed to about 25 μm, and used to form the balls. These particle balls are then subjected to a similar thermal process as the fiber/bead balls.

The interlocking of the fibers and beads keeps the granules from disassociating when wet, and absorb blood and other liquids well. The capillary action inside the granule assists in the transfer of liquid from one granule to the next. The granules should be expected to adsorb any liquid that will wet glass similarly, which includes, but is not limited to water based solutions or mixtures, alcohol solutions or mixtures, and petroleum based liquids or gels. From a clinical point of view, these granules are beneficial for blood loss control (hemostasis), adsorbing bone marrow aspirate, delivering drugs at the site of surgery, as a bone grafting/dental scaffold, as a soft tissue scaffold, or as components of a composite scaffold such as, but not limited to a bone wrap or wound dressing as exemplary applications. In clinical use, the unsintered fiber/bead balls may also be used to treat hard and soft tissue wounds.

When the starting material is 45S5 bioactive glass, 90% of the fiber ranges from 20 μm to 3 mm in length, 300 nm to 30 μm in diameter, with 90% of the beads in the range of 30 to 425 μm in diameter, with 10-50% fibers and 40-90% beads, preferably 25% fiber and 75% beads. The fiber and beads are gently mixed to form a fiber/bead agglomerate as shown in FIG. 8. The fiber/bead agglomerate may be used at this point for bone/tissue repair, or a component thereof or as a component of a putty, a cement or a tissue wrap. When used as a putty or cement, the agglomerate, being flexible, is simply pushed into place in a body cavity, where, over time, it will support tissue and/or bone in growths and acts as a restorable tissue/bone scaffold for the repair of damaged and/or diseased tissue/bone.

When sintering the fiber/bead balls, the agglomerates thus formed can be placed in a ceramic crucible 25 and heat treated at a temperature above the glass transition but below the glass melting temperature (Tm) for a matter of minutes, typically in a kiln or electric furnace at 900° F. to 1100° F. to form granules (FIGS. 2 and 3). The time at that temperature will vary dependent on the temperature. For instance at 900° F. about ten minutes will suffice, whereas less time is needed at higher temperatures. When only particles are used to form the balls, the result is depicted in FIG. 9. The granules are removed from the crucible and cooled rapidly on a thermally conductive material, such as a copper plate. A void in the shape of a cylinder 27 is left down the center of the crucible. This is done so that the fibers do not act as an insulator and block heat from reaching the material at the center of the crucible. Also, once the granules have bonded, they are difficult to remove without damaging the granules. The void allows heat to penetrate the granules evenly, and the core allows material to flow upon removal and eliminates damaging the granules prior to cooling below $T_g$. A schematic of the agglomerate loading in the crucible is shown in FIG. 5.

The sintered agglomerates are then passed through a propane/oxygen flame and quickly cooled, thereby forming a shielded glass scaffold, i.e., a ball having a fused glass exterior around an interior of fiber/granules. Dependent on the amount of time in the flame, the fused periphery may be made thicker or thinner.

EXAMPLE

Approximately 100 g of the crushed mixture is placed in an 8 inch stainless steel pan and sprayed with water enough to wet the surface of the powder. The sprayed mixture is then gently mixed allowing the wet particles to stick together. Agglomerates of powder can be made upwards of 1 cm, but the size of 1 to 6 mm is optimal. The agglomerates are collected and placed in a ceramic crucible, where they are heated to above the glass transition temperature but below the glass melt temperature for about ten minutes about 900° F. for 45S5, and then rapidly cooled to result in the sintered fiber/bead particle of FIGS. 2 and 3. In one embodiment the fiber/bead interlocking structure is directly heated in the flame, with no initial sintering. In another embodiment the sintered particle is directly heated in a flame. The fiber/bead interlocking structures of FIG. 8 (no sintering) are placed in the hopper 11 shown in FIG. 4 and with a vibratory feeder 12 directed into the flame 13 of a burner 15, the flame comprising mixed and combusted oxygen and propane. The flame settings vary with glass composition and burner size, but oxygen and propane are both required. The resulting temperature in the flame is therefore 3600° F. to 5100° F. Each agglomerate has the exterior fused in a fraction of a second while in the flame, leaving loose fibers and beads in the center. It is then blown into a collection tube 17 and cooled below the glass crystallization and glass transition temperature (Tg).

The embodiment utilizing a sintered fiber/bead interlocking structure may also be passed through a flame and result in an fused agglomerate with a variable thickness of the fused exterior as above, but the center is not loose.

The collection tube 17 is set at an angle between 15 and 45 degrees and fixed with a vibrator 19 to allow the fused granules to exit the tube into a collection pan 21 where the granules cool to room temperature. Depending on the flame depth and the drop distance of the agglomerate, the time each agglomerate is in the flame ranges from 1/100th to 1/4th of a second. The image of the resulting shielded granule is shown in FIG. 6. The rounded glassy surface is evident, but there is a fibrous core present in the center that will allow for tissue ingrowth and enhanced conversion compared to a solid glass particle or bead as shown in FIGS. 6 and 7. FIG. 6 is an SEM image, showing the surface of a shielded fiber/bead granule of about 1.1-2.0 mm diameter. The surface of the granule is covered with windows or pores that allows for tissue growth and fluid penetration. The approximate size range of the pores is ~10 μm to ~200 μm, which is sufficient for tissue infiltration. Due to the increased surface area of the internal porous microstructure, the rate of reaction of the porous granule is much higher than a solid glass sphere. FIG. 7 shows the porous fiber/bead granule of FIG. 6 formed from a non-sintered agglomerate and fractured in two; the external and internal microstructures are visible. In FIG. 7, the shield is the outer fused perimeter of the granule. There are loose fibers present at the bottom of FIG. 7 from fracturing the granule. The center of the fractured granule contains loose fibers and beads. By bonding the core through a longer or additional thermal treatment, the amount of bonding of the fibers and beads can be controlled. Further, an additional heat treatment for a sufficient length of time will crystallize the entire granule.

The broken scaffold of FIG. 7 shows the porous glassy shell covering the somewhat loose internal fiber network. The surface of the scaffolds has thin windows covering the surface that were formed at high temperature as the glass granules were melted and trapped gas (air) and made bubbles. The glass windows will quickly hydrate when in contact with liquids such as body fluids or blood and allow fluids to penetrate the scaffold and allow for growth of new tissues while improving the material properties and handling ability for clinicians.

It will be understood that the foregoing description is of preferred exemplary embodiments of the invention and that the invention is not limited to the specific forms shown or described herein. Various modifications may be made in the design, arrangement, and type of elements disclosed herein, as well as the steps of making and using the invention without departing from the scope of the invention as expressed in the appended claims.

The invention claimed is:

1. A method of preparing shielded glass scaffolds comprising the steps of:
   1) mixing bioactive glass beads with bioactive glass fibers to form compressible agglomerates;
   2) sintering the agglomerates
   3) dropping the sintered agglomerates through a flame with a temperature of about 3600° F. to 5100° F. to form a glassy exterior;
   4) cooling and collecting the resulting shielded glass scaffolds.

2. A method of preparing shielded glass scaffolds comprising the steps of:
   1) forming bioactive glass agglomerates from glass beads and glass fibers;
   2) placing in a crucible and heating to about 900° C. to about 1100° C. for a period of about ten to about twenty minutes, and then cooling to form sintered agglomerates,
   3) dropping the sintered agglomerates through a flame to form a glassy exterior and
   4) cooling to form shielded glass scaffolds.

3. The method of claim 2 wherein a central cylindrical axial opening is formed in the crucible.

4. The method of claim 2 wherein the glass powder is crushed to a mean particle size of about 25 μm with 90% less than 53 μm.

5. A method of preparing shielded glass scaffolds comprising the steps of:
   1) forming bioactive glass fiber and bioactive glass particle agglomerates;
   2) placing in a crucible and heating to above the glass transition temperature and below the glass melt temperature, and then cooling to form sintered agglomerates;
   3) dropping the sintered agglomerates through a flame with a temperature of about 3600° F. to 5100° F. to form a glassy exterior;
   4) cooling and collecting the resulting shielded glass scaffolds.

6. The method of claim 5, wherein the shielded glass scaffolds are given a further heat treatment to crystalize them.

7. The method of claim 5 wherein the glass fiber and particles are crushed to a mean particle size of about 25 μm with 90% less than 53 μm.

8. The method of claim 5 wherein a central cylindrical axial opening is formed in the crucible.

9. A method of preparing shielded a glass scaffold comprising the steps of:
   1) mixing bioactive glass beads with bioactive glass fibers to form compressible agglomerates;
   2) sintering the agglomerates
   3) dropping the sintered agglomerates through a flame with a temperature of about 3600° F. to 5100° F. to form a glassy exterior;
   4) cooling and collecting the resulting shielded glass scaffolds wherein said sintered agglomerates are utilized to form a scaffold selected from the group consisting of:
   a bone wrap,
   a composite,
   a bone or soft tissue putty,
   a hemostatic device,
   an orthopedic or spine related implant,
   an external bandage, and
   a bone cement or bone glue.

10. A method of preparing a shielded glass scaffold comprising the steps of:
   1) forming bioactive glass fiber and bioactive glass particle agglomerates;
   2) placing in a crucible and heating to above the glass transition temperature and below the glass melt temperature, and then cooling to form sintered agglomerates;
   3) dropping the sintered agglomerates through a flame with a temperature of about 3600° F. to 5100° F. to form a glassy exterior;
   4) cooling and collecting the resulting shielded glass scaffolds wherein said sintered agglomerates are utilized to form a scaffold selected from the group consisting of:
   a bone wrap,
   a composite,
   a bone or soft tissue putty,
   a hemostatic device,
   an orthopedic or spine related implant,
   an external bandage, and
   a bone cement or bone glue.

* * * * *